United States Patent [19]

Huhn et al.

[11] 4,324,903
[45] Apr. 13, 1982

[54] MALONIC ESTERS

[75] Inventors: Magda Huhn; Éva Somfai; Gábor Szabó; Gábor Resovszki; Livia Gneth née Zalántai, all of Budapest, Hungary

[73] Assignee: Chinoin Gyogyszer es Vegyeszeti Termekek Gyara RT., Budapest, Hungary

[21] Appl. No.: 698,063

[22] Filed: Jun. 21, 1976

[30] Foreign Application Priority Data

Jun. 20, 1975 [HU] Hungary ............................... CI 1592

[51] Int. Cl.$^2$ ...................... C07C 69/76; C07C 79/46; C07C 101/447
[52] U.S. Cl. ........................................ 560/82; 560/19; 560/20; 560/55; 260/347.4; 546/342; 549/79
[58] Field of Search ..................... 560/82; 260/475 SC

[56] References Cited

U.S. PATENT DOCUMENTS 2,419,865  4/1947  Weston et al. ......................... 560/82
3,824,275  7/1974  Kasubick ............................... 560/82

Primary Examiner—Paul J. Killos
Attorney, Agent, or Firm—Karl F. Ross

[57] ABSTRACT

A process for the preparation of new malonic esters of the formula:

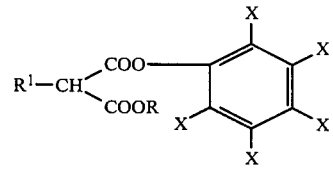

wherein R is a substituted or unsubstituted $C_1$ to $C_6$ alkyl, a substituted or unsubstituted aromatic ring, a heterocyclic ring, a cycloalkyl group, or a fused ring system; $R^1$ is hydrogen, lower alkyl, aralkyl, aralkyl substituted by halogen or alkyl or a substituted aromatic, cycloaliphatic or heterocyclic ring; and X is halogen.

5 Claims, No Drawings

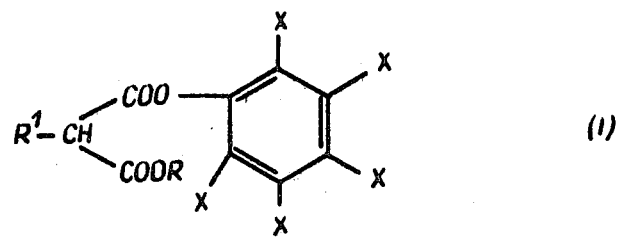
(I)
(II)
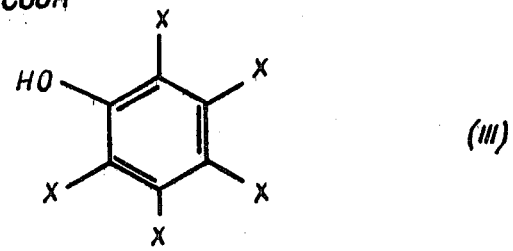
(III)
(IV)
(V)
(VI)
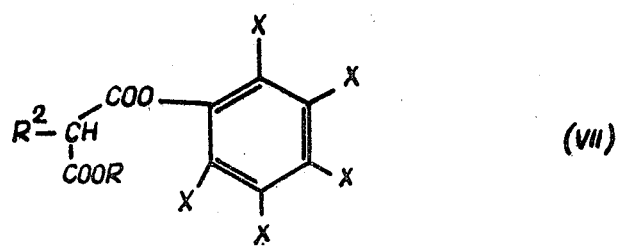
(VII)

MALONIC ESTERS

The present invention relates to malonic esters of the formula (I):

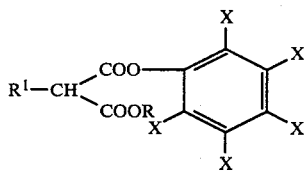 (I)

produced by reacting the reactive carbonic acid derivatives, preferably the halogenides of the malonic acid derivatives having the formula (II):

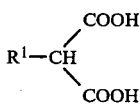 (II)

with phenol derivatives of the formula (III):

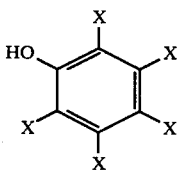 (III)

or their salts, or with the compounds of the formula (IV):

HO-R (IV)

or their salts, in an optional order, in one or more steps. In all of the above formulas
- R is a substituted or unsubstituted $C_{1-6}$ alkyl, a substituted or unsubstituted aromatic ring, a heterocyclic ring, a cycloalkyl group or a fused ring system,
- $R^1$ is hydrogen, a lower alkyl, unsubstituted aralkyl or aralkyl substituted with a halogen or an alkyl, a substituted aromatic, cycloaliphatic or heterocyclic ring,
- $R^2$ is a phenyl, thienyl, furyl or pyridyl grup, which can be substituted with a radical selected from the following group: halo, nitro, dialkylamino, alkoxy, trifluoromethyl,
- X and Y represent a halogen atom.

"Alkyl" as used herein is preferably $C_1$ to $C_6$ alkyl, "cycloalkyl" is preferably $C_3$ to $C_8$ cycloalkyl. The "aromatic ring" is preferably phenyl. The "heterocyclic ring" can be a 5 or 6 membered ring having 1, 2 or 3 N or O heteroatoms. "Cycloaliphatic" is preferably $C_3$ to $C_8$ cycloalkyl. The "fused ring system" is preferably naphthyl.

According to a preferred embodiment of the present invention, halomalonic acids of the formula (V):

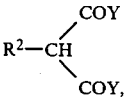 (V)

preferably chloro-, bromo, or iodomaonic acids can be used as starting materials.

Starting materials of the formula (II) can be prepared by methods known per se. E.g. dihalomalonic acids can be prepared starting from monosubstituted malonic acids, and halomalonic esters starting from hemi-esters, with a halogenating agent. Suitable halogenating agents are, for example, the following compounds: thionylchloride, Vilsmayer reagent, phosphorous oxychloride, phosphorous pentachloride. The resulting chloroacid is reacted with pentachlorophenol in a crude state, as the solvent and the excess of the halogenating agent are distilled off. As the acid binding agent a weak tertiary base is used.

The chloroacid is prepared at low temperature (below +50° C. to avoid the formation of ketene.

If phosphorous pentachloride is used for the preparation of the chloroacid, the phosphorous oxychloride formed during the reaction is distilled off, below +50° C. in vacuo. An analogous process is used if the chloroacid is prepared with excess of thionylchloride.

Preferably the pentachlorophenyl ester is produced in the presence of an acid-binding agent. For this purpose a "weak" tertiary base, for example, N,N-dimethylaniline can be utilized.

The reaction is preferably carried out in an inert solvent, which can be a halogenated solvent, e.g. methylene chloride, dichloroethane, carbontetrachloride, chloroform, benzene, xylene or acetonitrile.

Di- and monohaloderivatives, respectively, of the malonic acid derivatives are not purified before the esterification. The reaction is preferably carried out by adding the chloroacid to the salt of the N,N-dimethylaniline, but the reverse order is also expedient. There are also other salts suitable for this purpose.

When the esterification is carried out with a pentachlorophenyl salt at 10° to 15° C. the resulting dipentachlorophenyl ester immediately precipitates, but pentachlorophenyl esters of the various hemi-esters remain dissolved, and precipitate in a crystalline form first when the mixture is evaporated to dryness, and the residue is triturated with alcohol.

The dipentachlorphenyl esters of the substituted malonic acids and the mixed esters of the various hemi-esters with pentachloro phenol are insoluble in alcohol, and can be easily purified.

The hemi-esters of the substituted malonic acid may be prepared for example according to a process described in the U.S. Pat. No. 3,557,090. According to our invention dipentachlorophenyl esters of the substituted malonic acid can be prepared also starting from a compound of the formula II, with phosphorous oxychloride and pentachlorophenol, in the presence of pyridine. The compounds of the formula II are subjected to the above reaction preferably in the presence of a suitable solvent. If the reaction is carried out using pentachlorophenyl, the preferred solvents are acetone, acetonitrile or dichloromethane.

According to a further feature of the invention mixed esters can be preferably prepared by reacting the free hydroxyl group of the corresponding hemi-esters with a pentahalophenol or with a salt thereof, in the presence of a water trapping agent, preferably of dicyclohexylcarbodiimide. According to still a further feature of our invention mixed esters can be prepared in two steps. First one prepares di-pentahalophenyl ester by reacting a compound of the formula II or its haloderivative with pentahalophenol or a salt thereof, as described above I the second step the thus obtained compound is reacted with a compound of the formula R-OH, preferably in the presence of one mole of a tertiary base.

Very valuable intermediates can be obtained by reacting a reactive derivative of phenyl-malonic acid or phenyl-malonic acid substituted with an $R^1$ group, in the first step with benzylalcohol, 5-indanol, ethanol, methanol, phenol, allyl alcohol, trichloroethanol, p-nitro-benzyl-alcohols, and reacting the haloacids of the thus obtained hemi-esters with pentahalophenol, or a salt thereof, or reacting the hemi-esters with pentahalophenol, in the presence of dicyclohexyl-carbodiimide or phosphorous oxychloride. The $R^1$ group may be optionally substituted with a $C_{1-6}$ alkoxy group or with a halogen atom.

Malonic esters prepared according to the present invention are new compounds, and they are valuable intermediates of the production of malonic amides, in the presence of tertiary bases. These compounds can be utilized in various fields of organic chemistry, in all cases when a primary amino group is to be acylized, selectively, forming a peptide-bond, and when a further free carboxyl group is needed in the acylating moeity of the molecule.

Compounds of the present invention can be advantageously utilized for the acylation of sensitive amines, e.g. 6-amino-penicillic acid, 7-desacetyl-cephalosporanic acid, e.g. by substituting them for the acylating agents described in commonly owned application Ser. No. 598,692 filed July 24, 1975 (now abandoned) and its continuation in part application Ser. No. 812,735 filed Jul. 5, 1977.

The following starting materials are preferred: 3-thienyl- or 3-furyl- or 3-methoxy-phenyl- or 4-methoxy-phenyl- or 3-pyridyl- or o-chloro-phenyl- or o-bromo-phenyl- or p-chloro-phenyl or p-butoxyphenyl-dihalomalonic acids, or the corresponding hemi-esters.

Starting from the above compounds the suitably substituted derivatives can be prepared, which lead to valuable, well-known medicaments, when they are used for the acylation of the penam-or cephem-ring.

Acylating reaction of the primary amines and hydroxyl groups presumably takes part through ketene; thus our compounds are suitable for "in situ" preparation of ketenes.

The successful utilization of the monosubstituted malonic acid derivatives for N- and O-acylation at low temperature, in the presence of a teritiary base is a surprising fact, so much the more so that pentachlorophenyl esters of the disubstituted malonic acids of or the succinic acid are able to react with primary amines only in substitution reactions, at high temperature.

Up to now for similar N-acylation halomalonic acids were used. These compounds had a lot of disadvantages. The dichloromalonic acids are difficult to prepare in pure form, because they are susceptible to polymerization, and therefore they give a number of side-products, when used as acylating agents.

The halogenides of malonic acid and its derivatives decompose very easily, and therefore cannot be stored. Compounds prepared according to the present invention are very easy to store.

In new pentahalophenyl esters prepared according to our invention the phenyl group may be substituted with a fluro-, chloro-, bromo- or iodo-group. As it appears from the formulas and the examples, hemi-esters mixed-esters, and derivatives esterified on both carboxyl-function with a pentahalophenyl group are within the scope of the present invention.

Further details of the invention are illustrated by the following examples without limiting the scope of the invention to the examples:

EXAMPLE 1

Dispentachloro-phenyl phenylmalonate 72 g (0.4 mol) of phenylmalonic acid is in 600 ml. of methylene chloride, and 176 g. (0.8 mol) of phosphorous pentachloride is added. The mixture is stirred at room temperature for two hours, and methylene chloride and thereafter up to 50° C. phosphorous oxychloride are distilled off, the latter in vacuo.

The thus obtained residue is dissolved in 100 ml. of methylene chloride and the solution is added dropwise to the solution of 213 g. (0.8 mol) of pentachlorophenol and 80 ml. (0.8 mol) of pyridine in 800 ml. methanol, with stirring at room temperature. The precipitated white solid is stirred for 30 minutes, and thereafter it is filtered off. The obtained solid is washed with dry ethanol, and thus 215 g. of the named compound is obtained. Yield: 92%, melting point: 215° to 217° C.

Elemental analysis:

| Calculated: | C = 37.7 | H = 0.7 | Cl = 54.4% |
|---|---|---|---|
| Found: | C = 37.15 | H = 1.0 | Cl = 54.0% |

IR absorptions are: 1810 (ester), 1880 (ester), 1360, 1390 (pentachlorophenyl) $cm^{-1}$.

EXAMPLE 2

The dipentachloro-phenyl esters of the following malonic acid derivatives may be obtained using the procedure of the Example 1:

| $R^3$—CH(COO—$C_6Cl_5$)$_2$ | | C % | H % | Cl % | M.p. |
|---|---|---|---|---|---|
| 3-thienyl | calc. | 33.4 | | 52 | |
| | found | 33.82 | | 51.54 | |
| 3-furyl | calc. | 34.2 | 0.6 | 53.2 | |
| | found | 33.95 | 0.82 | 54.03 | |
| 3-methoxy-phenyl | calc. | 37.4 | 1.13 | 50.0 | |
| | found | 37.09 | 1.0 | 49.5 | |
| 4-methoxy-phenyl | calc. | 37.4 | 1.13 | 50.0 | |
| | found | 36.95 | 1.20 | 50.85 | |
| O-chloro-phenyl | calc. | 35.4 | 0.73 | 54.9 | |
| | found | 36.0 | 0.93 | 54.0 | 125–128° C. |
| O-bromo-phenyl | calc. | 33.4 | 0.66 | 41.8 | |
| | found | 32.9 | 0.59 | 42.3 | 128–130° C. |
| p-chloro-phenyl | calc. | 35.4 | 0.73 | 54.9 | |
| | found | 36.1 | 0.95 | 54.2 | 126–128° C. |
| 3-pyridyl | calc. | 35.5 | 0.74 | 52.4 | |
| | found | 34.9 | 0.69 | 51.9 | |

EXAMPLE 3

Following the procedure of the Examples 1 and 2 but using thienyl chloride as halogenating agent and benzene as solvent, 2 ml. of DMF is added. When the generation of hydrochloric acid completes the benzene and the excess of thionychloride are distilled off in vacuo, and the residue is added to the solution of the pentachlorophenol- pyridine salt in benzene. When the reaction terminates ethanol is added to the dense mixture containing precipitate to dissolve the resulted pyridine salts, and thereafter the substance is filtered off and washed with alcohol.

Products identical with the above ones are obtained. Characterizing IR absorptions for all of the products are: 1810 (ester), 1880 (ester), 1360 (pentachlorophenyl), 1390 (pentachlorophenyl) cm$^{-1}$.

EXAMPLE 4

Dipentachlorophenyl malonate 14 g. (0.1 mol) of dichloromalonic acid (Staudinger J. 41, [1908]446 ) is dissolved in 50 ml. of methylene chloride, and the thus obtained solution is added to the solution of 53 g. (0.2 mol) of pentachlorophenol and 16 ml. (0.2 mol) pyridine on 300 ml dichloromethane dropwise, at +15° C. The precipitated solid is filtered off, washed with alcohol whereupon 42 g. of an amorphous substance (named compound) is obtained. Melting point: 195° to 197° C. IR absorptions are: 1790 (ester), 1360 (pentachlorophenyl), 1810 (ester), 1390 (pentachlorophenyl)cm$^{-1}$

EXAMPLE 5

Dipentachlorophenyl methylmalonate 19.4 g. (0.1 mol) of diethylmalonic acid chloride is dissolved in 70 ml. of methylene chloride. The solution is added dropwise to the solution of 53 g. (0.1 mol) of pentachlorophenol in 16 ml. (0.2 mol) of pyridine in 300 ml. of dichloromethane. The precipitated solid is filtered off. washed with alcohol, whereupon 50 g. (77%) of the named compound is obtained. Melting point: 165° to 168° C.

Elemental analysis:

| Calculated: | C = 34.70 | H = 1.52 | Cl = 54.00% |
| Found: | C = 34.83 | H = 1.48 | Cl = 54.39% |

IR-absorptions are: 1775 (ester), 1390 (pentachlorophenyl) cm$^{-1}$.

EXAMPLE 6

Dipentachloro-phenyl phenylmalonate 4.5 g. of phenylmalonic acid is suspended in 100 ml. of cidhloromethane, the suspension is cooled to 0° C. and 13 g. (0.05 mol) of pentachlorophenol and 9 ml. (0.1 mol) or pyridine are added, resulting in the formation of a clear solution.

2.1 ml. of phosphorous oxychloride is added to the reaction mixture dropwise, at 0° C., the mixture is stirred for 2 hours, filtered at 0° C., and the obtained solid is washed with alcohol. Thus 7 g. of the named compound, melting at 210° to 215° C. is obtained. IR-absorptions are observed at 1810 (ester). 1880 (ester), 1360, 1390 (pentachlorophenyl) cm$^{-1}$.

EXAMPLE 7

Benzyl-pentachlorophenyl phenylmalonate 32.1 g. (0.12 mol) of hemi-benzyl phenylmalonate is dissolved in 100 ml. of methylene chloride, and 22 ml. of thionyl chloride and 3 drops of DMF are added.

The solution is refluxed for 2 hours. The solvent and the excess of thionychloride are distilled off, and the remaining chloroacid is diluted with 5 ml. of dichloromethane. The thus obtained mixture is added dropwise to the solution of 31.9 g. (0.12 mol) pentachlorophenol and 9.6 ml. of pyridine, in 200 ml. dichloromethane at 10° C. The solution is stirred for 30 minutes at room temperature, the precipitated by-product is filtered off, the dichloromethane is evaporated, and the residue is triturated with dry alcohol. Filtration of the precipitated crystallines product from the cold solution yields 38.40 g. (62%) of the named compound.

Melting point = 129° to 132° C.

Elemental analysis:

| Calculated: | C = 51.16, | H = 2.51, | O = 12.40 | Cl = 33.90% |
| Found: | C = 51.43, | H = 2.28, | 0 = 12.47 | Cl = 34.50% |

EXAMPLE 8

Ethyl-pentachlorophenyl phenylmalonate 10.40 g. (0.05 mol) of hemi-ethyl phenylmalonate is dissolved in 50 ml. of methylene chloride, and 8 ml. of thionyl chloride and one drop of dimethyl formamide are added dropwise to the solution. The mixture is stirred for 2 hours at 45° to 50° C. The solvent and the excess of the thionyl chloride are distilled off, and the chloroacid is diluted with 20 ml. of dichloromethane, and thereafter is added to the solution of 13.30 g. (0.05 mol) of pentachlorophenol, and 4 ml. (0.05 mol) of pyridine in 80 ml. of dichloromethane. The solution is stirred at room temperature for one and a half hours. The dichloromethane is washed with 2 N hydrochloric acid and water, dried and evaporated. The residue is taken up with dry alcohol, and the precipitated crystals are filtered off from the cold solution. Thus 14.40 g. (63.50%) of the named compound are obtained. Melting point = 95° to 97° C.

Elemental analysis:

| Calculated: | C = 44.93, | H = 2,42, | O = 14.09 | Cl = 38,50% |
| Found: | C = 44.62, | H = 2.42, | O = 13.65 | Cl = 37.92% |

EXAMPLE 9

Indanyl-pentachlorophenyl phenylmalonate 14.80 g. (0.05 mol) of hemi-indanyl phenylmalonate is dissolved in 150 ml. of dichloromethane, and 8 ml. of thionylchloride and one drop of dimethyl formamide are added dropwise. The solution is stirred at 45° to 50° C. for 2 hours. The solvent and the excess of thionyl chloride are distilled off, and the chloroacid is diluted with 30 ml. of dichloromethane and the mixture is added dropwise to the solution of 13.3 g. (0.05 mol) of pentachlorophenol and 4 ml. of pyridine in 100 ml. of dichloromethane. The solution is stirred at ambient temperature for two hours. The precipitated by-product is filtered off. The dichloromethane is shaken with 2 N hydrochloric acid and water, dried, and the solvent is evaporated. The residue is triturated with dry alcohol. The precipitated crystals are filtered off from the cold solution. Thus 16.90 g. of the pure compound named is obtained, melting at 85° to 88° C.

Elemental analysis:

| Calculated: | C = 53,12, | H = 2.77, | O = 11,80, | Cl = 32.20% |
| Found: | C = 52.94, | H = 2.65, | O = 10.95, | Cl = 31.80% |

EXAMPLE 10

Following the procedure described in the previous example the following hemi-pentachlorophenyl esters can be also obtained: $C_6H_5-CH(COOR^4)COOC_6Cl_5$

| R⁴ | | % C | % H | % Cl |
|---|---|---|---|---|
| Phenacyl | calculated | 50.73 | 2.39 | 32.00 |
|  | found | 50.21 | 2.11 | 30.08 |
| p-nitro- | calculated | 46.90 | 2.05 | 28.90 |
| phenacyl | found | 45.92 | 1.85 | 27.80 |
| Trichloro- | calculated | 36.68 | 1.43 | 50.36 |
| ethyl | found | 35.98 | 1.12 | 49.98 |

EXAMPLE 11

Dipentachlorophenyl malonate 5.0 g. (0.05 mol) of malonic acid is suspended in 180 ml. of acetone, 26 g. (0.1 mol) of pentachlorophenol and 9 ml. (0.1 mol) of pyridine are added to the suspension, whereupon clear solution is obtained. The solution is cooled to 0° C., 8.4 ml. of phosphorous oxychloride is added dropwise, and the mixture is stirred at 0° C. for one hour, and thereafter at +10° C. for one hour. The precipitated solid is filtered off, and washed with cold alcohol. Thus 14 g. of the named compound is obtained as a white amorphous powder. Melting point=170° C. to 172° C.

IR peaks: 1800, 1780 (ester), 1360, 1390 (pentachlorophenyl)cm⁻¹.

Elemental analysis:

| Calculated: | C = 30.1 | Cl = 58% |
|---|---|---|
| Found: | C = 30.47 | Cl = 59.3% |

EXAMPLE 12

Dipentachlorophenyl allylmalonate 41.6 g. (0.2 mol) of phosphorous pentachloride is suspended in 200 ml of benzene, and 14 g. (0.1 mol) of allylmalonic acid is added in small portions at +10° C. The mixture is heated to 50° C. to 60° C. till the generation of hydrochloride terminates, the solvent and the oxychloride are evaporated in vacuo, the chloroacid (15.9 g.) is dissolved in 50 ml. of carbontetrachloride and is added dropwise to the solution of 53 g. (0.2 mol) of pentachlorophenol and 16 ml. (0.2 mol) of pyridine in 500 ml. of carbontetrachloride. The precipitated solid is filtered off, and washed with carbontetrachloride and alcohol. The thus obtained amorphous substance is dried. 46.6 g. of the named compound is obtained, melting at 155° C. to 158° C.

IR absorptions are: 1800–1780 (ester), 1340–1360 (pentachlorophenyl)cm⁻¹.

Elemental analysis:

| Calculated: | C = 34.00 | Cl = 55.5% |
|---|---|---|
| Found: | C = 33.85 | Cl = 54.95% |

EXAMPLE 13

Dipentachlorophenyl ethylmalonate 41.6 g. (0.2 mol) of phosphorus pentachloride is suspended in 150 ml. of benzene and 12.0 g. (0.1 mol) of ethylmalonic acid is added in small portions. The mixture is stirred at 50° C. for two hours, the benzene is distilled off, and the phosphorous oxychloride is dissolved in 50 ml. of carbontetrachloride. Thereafter the resulted solution is added dropwise to the solution of 53.2 g. (0.2 mol) of pentachlorophenol and 16 ml. (0.2 mol) pyridine in 150 ml. of carbontetrachloride. The reaction mixture is stirred at room temperature, and the solid is filtered off, suspended with alcohol on the filter, and washed with alcohol. 51.0 g. (81%) of the named compound is obtained as a white amorphous powder, melting at 148° C. to 150° C.

IR peaks: 1800 (ester), 1780 (ester) cm⁻¹.

Elemental analysis:

| Calculated: | C = 32.7 | H = 0.96 | Cl = 56.09% |
|---|---|---|---|
| Found: | C = 32.1 | H = 0.80 | Cl = 55.50% |

EXAMPLE 14

Dipentachlorophenyl benzylmalonate 105 g. (0.52 mol) of phosphorous pentachloride are dissolved in 600 ml. of benzene and 50 g. (0.26 mol) of benzylmalonic acid is added. The solution is kept at 50° C. till the generation of hydrochloric acid terminates, thereafter the benzene and phosphorous oxychloride are distilled off. The residue is dissolved in 50 ml. of carbontetrachloride and it is added dropwise to the solution of 143 g. (0.5 mol) of pentachlorophenyl and 42 ml (0.5 mol) pyridine in 500 ml of carbontetrachloride. The precipitated substance is filtered off, washed with alcohol. Thus 80 g. (50%) of the named compound is obtained.

IR absorption is observed at 1800 (ester) cm⁻¹.

Elemental analysis:

| Calculated: | C = 38.40 | H = 1.27 | Cl = 51.50% |
|---|---|---|---|
| Found: | C = 39.00 | H = 1.30 | Cl = 50.90% |

EXAMPLE 15

Dipentachlorophenyl furylmethylmalonate 41.6 g. (0.2 mol) of phosphorous pentachloride is suspended in 150 ml. of benzene and 18 g. (0.1 mol) of furylmethyl malonic acid is added with cooling. The mixture is heated to 50° C. to 60° C., and kept at this temperature till the generation of hydrochloric acid terminates. The benzene and phosphorous oxychloride are distilled off, the remaining chloroacid is dissolved in 50 ml. of carbontetrachloride and is added to the solution of 52.0 g. (0.2 mol) of pentachlorophenol and 18 ml. of pyridine in 200 ml. of carbontetrachloride. The precipitated solid is filtered off, and washed with alcohol.

IR absorption is observed at 1790 (ester) cm⁻¹.

Elemental analysis:

| Calculated: | C = 35.10 | Cl = 54.0% |
|---|---|---|
| Found: | C = 34.90 | Cl = 53.50% |

EXAMPLE 16

Phenylpentachlorophenyl phenylmalonate 25 g. (0.1 mol) of hemi-phenyl phenylmalonate is suspended in 200 ml. of benzene and 20 ml. of thionyl chloride and 4 to 5 drops of dimethyl formamide are added. The mixture is stirred at 50° C. to 60° C. till solution is complete. The solution is left at the previous temperature for an other hour, thereafter the solvent is evaporated, the residue is taken up in 50 ml. of carbontetrachloride, and it is added dropwise to the solution of 26.6 g. (0.1 mol) of pentachlorophenol and 8 ml. (0.1 mol) of pyridine in 300 ml. of carbontetrachloride at 25° C. to 30° C. The precipitated pyridine chlorohydrate is washed with 2-fold 100 ml. of N hydrochloric acid, and then with 100 ml. of water. The carbontetrachloride solution is evaporated after drying. The residue is triturated with 100 ml. of ethanol at +5° C. to +10° C., and thereafter it is filtered off. 39 g. of the named compound is obtained as a white amorphous powder. Yield: 75%, melting point: 115° C. to 118° C.

IR absorptions are: 1800 (ester), 1760 (ester)cm$^{-1}$.
Elemental analysis:

| Calculated: | C = 49.5  | H = 2.17 | Cl = 35.00% |
| Found:      | C = 49.75 | H = 2.36 | Cl = 36.00% |

EXAMPLE 17

2,4-Xylenyl-pentachlorophenyl phenylmalonate 10 g. (0.355 mol) of hemi-2,4-xelyl phenylmalonate is dissolved in 50 ml. of carbontetrachloride, and 9.3 g. (0.035 mol) of pentachlorophenol and 7.35 g. of DCC in 50 ml. of carbontetrachloride are added dropwise. The mixture is stirred at room temperature for 3 hours and thereafter it is filtered. The solution is evaporated, and the residue is triturated with alcohol. Thus 8 g. of the title compound is obtained. Yield: 50%, melting point: 108° C. to 110° C.
Elemental analysis:

| Calculated: | C = 52.0  | H = 2.83 | Cl = 33%    |
| Found:      | C = 51.91 | H = 2.90 | Cl = 33.54% |

EXAMPLE 18

3,4-xylenyl-pentachlorophenyl phenylmalonate 8.5 g. (0.03 mol) of hemi-3,4-xylenyl phenylmalonate is suspended in 100 ml. of benzene, 4 to 5 drops of dimethyl formamide and 3.2 ml. (0.045 mol) of thionylchloride are added. The mixture is stirred for two hours at 45° C. to 50° C., and the thionyl chloride and benzene are distilled off under nitrogene atmosphere. The residue is diluted with 50 ml. of carbontetrachloride and is added dropwise to the solution of 7.98 g. (0.03 mol) pentachlorophenol and 2.4 ml. (0.03 mol) of pyridine in 100 ml. of carbontetrachloride. The precipitated pyridine chlorohydrate is washed with 50 ml. of 2 N hydrochloric acid. The solution is evaporated, and the residue is triturated with cold alcohol. Thus 10 g. (67%) of the title compound is obtained, melting at 125° C. to 128° C.

IR absorptions are: 1800 (pentachlorophenyl), 1760 (3,4-xylenyl)cm$^{-1}$.
Elemental analysis:

| Calculated: | C = 51.00 | H = 2.83 | Cl = 33%    |
| Found:      | C = 51.09 | H = 2.40 | Cl = 34.54% |

EXAMPLE 19

Indanyl-pentachlorophenyl phenylmalonate 23.68 g. (0.08 mol) of hemi-indanyl phenylmalonic acid is dissolved in 200 ml. of benzene, 8.8 ml. (0.12 mol) of thionylchloride and 6 to 8 drops of dimethylformamide are added, and the mixture is stirred at 45° C. to 50° C. for two hours till the generation of hydrochloric acid gas terminates. Benzene and the excess of thionyl chloride are distilled off in high vacuo. The residue is dissolved in 50 ml. of carbontetrachloride and the thus obtained solution is added dropwise to the solution of 21.28 g. (0.08 mol) pentachlorophenol and 150 ml. of carbontetrachloride in 6.4 ml. (0.08 mol) of pyridine. The solution is stirred for one hour at room temperature. Thereafter it is decomposed with 100 ml. of 2 N hydrochloric acid, and is washed with 3×50 ml. of 2 N hydrochloric acid and 1×50 ml. of sodium chloride solution. Carbon tetrachloride and the solvent are evaporated, and the residue is taken up with 80 ml. of absolute alcohol. When cooling the mixture, the hemi-ester precipitates, it is filtered off and washed with a small amount of cold alcohol. Thus 32.5 g. (75%) of the named compound is obtained, melting at 118° to 120° C.

IR absorptions are: 1790 (pentachlorophenyl ester), 1760 (indanyl ester) cm$^{-1}$.
Elemental analysis:

| Calculated: | C = 53.1  | H = 2.77 | Cl = 32.2%  |
| Found:      | C = 53.45 | H = 2.60 | Cl = 33.07% |

EXAMPLE 20

Indanyl-pentachlorophenyl phenylmalonate 11 g. (0.035 mol) of hemi-indanyl phenylmalonate is dissolved in 50 ml. of carbon tetrachloride and the solution of 9.3 g. (0.03 mol) of pentachlorophenol and 7.35 g. of DCC (dicyclohexylcarbodiimide) in 50 ml. of carbon tetrachloride is added dropwise. The solution is stirred for 2 hours at room temperature, and the precipitated dicyclohexylurea is filtered off. The carbon tetrachloride solution is evaporated in vacuo and the residue is triturated with cold alcohol and filtered off. After drying 14 g. (75%) of the named compound is obtained, melting at 118° to 120° C.

IR absorptions are: 1790 (pentachlorophenyl ester), 1760 (indanyl ester) cm$^{-1}$.

EXAMPLE 21

β-naphthyl-pentachlorophenyl phenylmalonate 9 g. (0.03 mol) of hemi-naphthyl phenylmalonate is dissolved in 50 ml. of carbontetrachloride and the solution of 7.85 g. (0.03 mol) pentachlorophenol and 6.4 g. (0.03 mol) of DCC in 50 ml. of carbontetrachloride is added dropwise, with stirring at room temperature. The mixture is stirred for two hours, the precipitated DCU is filtered off, and the carbontetrachloride solution is evaporated, the residue is triturated with alcohol, and thus 12 g. (70%) of the named compound is obtained, melting at 136° C. to 137° C.

IR absorptions are: 1800 (pentachlorophenyl ester), 1760 (β-naphthyl ester)cm$^{-1}$.

EXAMPLE 22

Phenacyl-pentachlorophenyl phenylmalonate 9 g. (0.03 mol) of hemi-phenacyl phenylmalonate is dissolved in 50 ml. of carbontetrachloride, and the solution of 7.85 g. (0.03 mol) of pentachlorophenol and 6.4 g. (0.03 mol) DCC in 50 ml of carbontetrachloride are added dropwise, with stirring at room temperature. The mixture is stirred for two hours, the resulted DCU is filtered off, and the carbontetrachloride solution is evaporated. The residue is triturated with alcohol. Thus 12 g. (70%) of the named compound is obtained.

IR absorption is observed at: 1790 (pentachlorophenyl ester)cm$^{-1}$.

Elemental analysis:

| Calculated: | C = 50.73 | H = 2.39 | Cl = 32.20% |
|---|---|---|---|
| Found: | C = 50.21 | H = 2.11 | Cl = 30.08% |

EXAMPLE 23

The following hemi-pentachlorophenyl phenylmalonate compounds may be prepared using the procedure of the previous example:

| R' | | % C | % H | % Cl |
|---|---|---|---|---|
| p-nitro phenacyl | calculated | 46.90 | 2.05 | 28.90 |
| | found | 45.92 | 1.85 | 27.80 |
| trichloro- ethyl | calculated | 36.68 | 1.43 | 50.36 |
| | found | 35.98 | 1.12 | 49.98 |

We claim:

1. A compound of the formula:

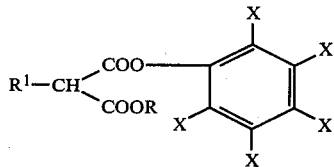

wherein
R is an alkyl or halosubstituted alkyl of 1 to 6 carbon atoms wherein the halo is fluoro, chloro, bromo or iodo, or
R is unsubstituted aromatic, or
R is a fused homocyclic ring system;
R$^1$ is aryl or aralkyl, unsubstituted or substituted by fluoro, chloro, bromo or iodo, nitro, dialkylamino, alkoxy or trifluoromethyl, the alkyl being C$_1$ to C$_6$; and
X is a halogen atom selected from the group consisting of fluorine, chlorine, bromine or iodine.

2. A compound of the formula:

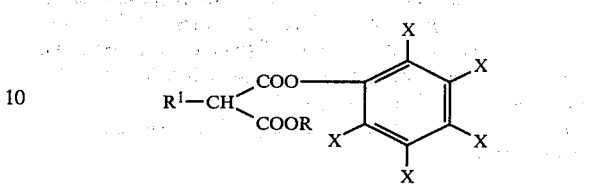

wherein
R is phenyl substituted with fluoro, chloro, bromo or iodo;
R$^1$ is phenyl; and
X is a halogen atom selected from the group consisting of fluorine, chlorine, bromine or iodine.

3. The compound defined in claim 18 wherein X is chloro.

4. Dipentachlorophenyl-phenylmalonate.

5. A compound selected from the group consisting of:
dipentachlorophenyl-phenylmalonate;
pentachlorophenyl-benzyl-phenylmalonate;
pentachlorophenyl-phenyl-phenylmalonate;
pentachlorophenyl-naphthyl-phenylmalonate;
pentachlorophenyl-phenacyl-phenylmalonate;
pentachlorophenyl-2,4-xylenyl-phenylmalonate;
pentachlorophenyl-3,4-xylenyl-phenylmalonate;
pentachlorophenyl-indanyl-phenylmalonate;
dipentachlorophenyl-3-methoxyphenylmalonate;
dipentachlorophenyl-4-methoxyphenylmalonate;
dipentachlorophenyl-o-chlorophenylmalonate;
dipentachlorophenyl-o-bromophenylmalonate;
dipentachlorophenyl-p-chlorophenylmalonate;
pentachlorophenyl-p-nitrophenacyl-phenylmalonate; and
dipentachlorophenyl-benzylmalonate.

* * * * *